United States Patent
Mylari

(10) Patent No.: US 6,720,348 B2
(45) Date of Patent: Apr. 13, 2004

(54) COMBINATION OF GABA AGONISTS AND ALDOSE REDUCTASE INHIBITORS

(75) Inventor: Banavara L. Mylari, Waterford, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/997,039

(22) Filed: Nov. 29, 2001

(65) Prior Publication Data

US 2002/0077319 A1 Jun. 20, 2002

Related U.S. Application Data

(60) Provisional application No. 60/250,448, filed on Nov. 30, 2000.

(51) Int. Cl.$^7$ .................. A61K 31/42; A61K 31/495; A61K 31/505; A61K 31/44; A61K 31/445
(52) U.S. Cl. .................. 514/380; 514/248; 514/256; 514/258; 514/259; 514/287; 514/326; 514/369
(58) Field of Search .................. 514/380, 387, 514/369, 259, 248, 326, 258, 256

(56) References Cited

U.S. PATENT DOCUMENTS

| | | | |
|---|---|---|---|
| 3,242,190 A | 3/1966 | Hafliger et al. | 260/307 |
| 3,471,548 A | 10/1969 | Keberle et al. | 260/471 |
| 3,960,927 A | 6/1976 | Metcalf et al. | 260/471 A |
| 4,024,175 A * | 5/1977 | Satzinger et al. | 260/468 J |
| 4,094,992 A | 6/1978 | Kaplan et al. | 424/324 |
| 4,130,714 A | 12/1978 | Sarges | 548/309 |
| 4,251,528 A * | 2/1981 | Brittain et al. | 424/250 |
| 4,370,338 A | 1/1983 | Mizoule | 424/270 |
| 4,436,745 A | 3/1984 | York, Jr. | 424/273 R |
| 4,438,272 A | 3/1984 | York, Jr. | 548/308 |
| 4,464,382 A | 8/1984 | Tanouchi et al. | 424/270 |
| 4,513,006 A | 4/1985 | Maryanoff et al. | 514/23 |
| 4,540,704 A | 9/1985 | Ueda et al. | 514/389 |
| 4,600,724 A | 7/1986 | Sestanj et al. | 514/510 |
| 4,602,017 A | 7/1986 | Sawyer et al. | 514/242 |
| 4,734,419 A | 3/1988 | Hashimoto et al. | 514/259 |
| 4,771,050 A | 9/1988 | Meguro et al. | 514/224.2 |
| 4,771,052 A * | 9/1988 | Schonafinger et al. | 514/287 |
| 4,791,126 A | 12/1988 | Tanouchi et al. | 514/369 |
| 4,831,045 A * | 5/1989 | Tanouchi et al. | 514/369 |
| 4,883,410 A | 11/1989 | Goddard et al. | 417/69 |
| 4,883,800 A * | 11/1989 | Hashimoto et al. | 514/259 |
| 4,939,140 A | 7/1990 | Larson | 514/222 |
| 4,980,357 A | 12/1990 | Goldstein et al. | 514/278 |
| 4,996,204 A * | 2/1991 | Mylari et al. | 514/248 |
| 5,010,090 A * | 4/1991 | Gronvald et al. | 514/326 |
| 5,037,831 A | 8/1991 | Malamas | 514/278 |
| 5,066,659 A | 11/1991 | Lipinski | 514/278 |
| 5,236,945 A * | 8/1993 | Mylari et al. | 514/403 |
| 5,252,572 A * | 10/1993 | Hermecz et al. | 514/258 |
| 5,270,342 A | 12/1993 | Brittain et al. | 514/617 |
| 5,430,060 A | 7/1995 | Brittain et al. | 514/617 |
| 5,447,946 A | 9/1995 | Kurono et al. | 514/389 |
| 5,728,704 A * | 3/1998 | Mylari et al. | 514/256 |
| 6,028,214 A * | 2/2000 | Silverman et al. | 560/188 |
| 6,294,538 B1 * | 9/2001 | Mylari | 514/252.14 |
| 6,350,769 B1 * | 2/2002 | Kaufman et al. | 514/380 |

FOREIGN PATENT DOCUMENTS

| | | | |
|---|---|---|---|
| WO | WO 0045818 | 8/2000 | A61K/31/505 |
| WO | WO 0050034 | 8/2000 | A61K/31/42 |

* cited by examiner

*Primary Examiner*—Kevin E. Weddington
(74) *Attorney, Agent, or Firm*—Peter C. Richardson; Gregg C. Benson; William F. Mulholland

(57) ABSTRACT

This invention relates to pharmaceutical compositions comprising combinations of a GABA agonist, a prodrug thereof or a pharmaceutically acceptable salt of said GABA agonist or said prodrug and an ARI, a prodrug thereof or a pharmaceutically acceptable salt of said ARI or said prodrug, kits containing such combinations and methods of using such combinations to treat mammals, including humans, suffering from diabetic complications such as diabetic neuropathy, diabetic nephropathy, diabetic cardiomyopathy, diabetic retinopathy, diabetic microangiopathy, diabetic macroangiopathy, cataracts or foot ulcers.

27 Claims, No Drawings

COMBINATION OF GABA AGONISTS AND ALDOSE REDUCTASE INHIBITORS

CROSS-REFERENCE TO RELATED APPLICATIONS

The present application is a U.S. non-provisional application. This application claims the benefit of U.S. No. 60/250,448 filed on Nov. 30, 2000, under 35 USC 119(e).

FIELD OF THE INVENTION

This invention relates to pharmaceutical combinations of a γ-aminobutyric acid (GABA) agonist, a prodrug thereof or a pharmaceutically acceptable salt of said GABA agonist or said prodrug and an aldose reductase inhibitor (ARI), a prodrug thereof or a pharmaceutically acceptable salt of said ARI or said prodrug, kits containing such combinations and methods of using such combinations to treat mammals, including humans, suffering from diabetic complications such as, inter alia, diabetic neuropathy, diabetic nephropathy, diabetic cardiomyopathy, diabetic retinopathy, diabetic microangiopathy, diabetic macroangiopathy, cataracts or foot ulcers. This invention also relates to additive and synergistic combinations of a GABA agonist, a prodrug thereof or a pharmaceutically acceptable salt of said GABA agonist or said prodrug and an ARI, a prodrug thereof or a pharmaceutically acceptable salt of said ARI or said prodrug, whereby those additive and synergistic combinations are useful in treating mammals, including humans, suffering from diabetic complications such as, inter alia, diabetic neuropathy, diabetic nephropathy, diabetic cardiomyopathy, diabetic retinopathy, diabetic microangiopathy, diabetic macroangiopathy, cataracts or foot ulcers.

BACKGROUND OF THE INVENTION

GABA is the major inhibitory neurotransmitter in the mammalian central nervous system. Its receptors have been divided into two main types. The more prominent GABA receptor subtype, the $GABA_A$ receptor, is a ligand-gated $Cl^-$ ion channel that is opened after release of GABA from presynaptic neurons. A second receptor, the $GABA_B$ receptor, is a member of the G protein-coupled receptor family coupled both to biochemical pathways and to regulation of ion channels. (Goodman and Gilman's The Pharmacological Basis of Therapeutics, McGraw-Hill, New York, N.Y., $9^{th}$ Edition, (1996).

By gating negative chloride ($Cl^-$) ions into the interior of cells, GABA inhibits the presynaptic release of neurotransmitter due to a positive voltage polarization pulse. Such inhibition is extremely common: GABA receptors can be found in 60–80% of central nervous system neurons. Subtypes of GABA receptors can be activated by the mushroom toxin muscimol (at $GABA_A$) as well as the antispasmodic amino acid baclofen ($GABA_B$). These compounds directly mimic the action of GABA at the receptor. Allosteric facilitation of GABA receptors occurs at several distinct sites; the compounds which bind there are used as sedatives and anxiolytics. Progabide is a prodrug which decomposes to GABA after crossing the blood/brain barrier into the central nervous system. Vigabatrin (gamma-vinyl-GABA) promotes binding of GABA by inhibiting GABA-aminotransferase (GABA-T), the enzyme responsible for degrading GABA in the synapse.

GABA agonists well known in the art include muscimol, progabide, riluzole, baclofen, gabapentin (Neurontin®), vigabatrin, valproic acid, tiagabine (Gabitril®), lamotrigine (Lamictal®), pregabalin, phenytoin (Dilantin®), carbamazepine (Tegretol®), topiramate (Topamax®) and analogs, derivatives, prodrugs and pharmaceutically acceptable salts of those GABA agonists. It will be recognized by those skilled in the art in light of this disclosure that other GABA agonists are also useful in the combinations, pharmaceutical compositions, methods and kits of this invention. GABA agonists have been disclosed to be useful in antiseizure therapy for central nervous system disorders such as epilepsy, Huntington's chorea, cerebral ischemia, Parkinson's disease, tardive dyskinesia and spasticity. GABA agonists have also been disclosed to be useful as antidepressants, anxiolytics and antipsychotics. Further, GABA agonists have been disclosed to have utility in the treatment of pain.

Aldose reductase inhibitors function by inhibiting the activity of the enzyme aldose reductase, which is primarily responsible for regulating the reduction of aldoses, such as glucose and galactose, to the corresponding polyols, such as sorbitol and galactitol, in humans and other animals. In this way, unwanted accumulations of galactitol in the lens of galactosemic subjects and of sorbitol in the lens, peripheral nervous cord and kidneys of various diabetic subjects are prevented or reduced. Accordingly, aldose reductase inhibitors are of therapeutic value for controlling certain diabetic complications, e.g., diabetic neuropathy, diabetic nephropathy, diabetic cardiomyopathy, myocardial infarction, cataracts and diabetic retinopathy.

SUMMARY OF THE INVENTION

This invention is directed to pharmaceutical compositions comprising:

a. an amount of a GABA agonist, a prodrug thereof or a pharmaceutically acceptable salt of said GABA agonist or said prodrug;

b. an amount of an ARI, a prodrug thereof or a pharmaceutically acceptable salt of said ARI or said prodrug; and, optionally, c. a pharmaceutically acceptable vehicle, carrier or diluent.

This invention is also directed to kits for achieving a therapeutic effect in a mammal comprising:

a. an amount of a GABA agonist, a prodrug thereof or a pharmaceutically acceptable salt of said GABA agonist or said prodrug and a pharmaceutically acceptable vehicle, carrier or diluent in a first unit dosage form;

b. an amount of an ARI, a prodrug thereof or a pharmaceutically acceptable salt of said ARI or said prodrug and a pharmaceutically acceptable vehicle, carrier or diluent in a second unit dosage form; and c. a container.

This invention is also directed to methods for treating a mammal in need of therapeutic treatment comprising administering to said mammal (a) an amount of a first compound, said first compound being a GABA agonist, a prodrug thereof or a pharmaceutically acceptable salt of said GABA agonist or said prodrug; and (b) an amount of a second compound, said second compound being an ARI, a prodrug thereof or a pharmaceutically acceptable salt of said ARI or said prodrug;

wherein said first compound and said second compound are each optionally and independently administered together with a pharmaceutically acceptable vehicle, carrier or diluent.

This invention is also directed to methods for treating a mammal in need of therapeutic treatment comprising administering to said mammal a pharmaceutical composition comprising (a) an amount of a first compound, said first compound being a GABA agonist, a prodrug thereof or a pharmaceutically acceptable salt of said GABA agonist or said prodrug; and (b) an amount of a second compound, said second compound being an ARI, a prodrug thereof or a pharmaceutically acceptable salt of said ARI or said prodrug; and, optionally, (c) a pharmaceutically acceptable vehicle, carrier or diluent.

The methods of this invention include therapeutic treatment of diabetic complications. Diabetic complications which may be treated by the methods of this invention include, inter alia, diabetic neuropathy, diabetic nephropathy, diabetic cardiomyopathy, diabetic retinopathy, diabetic microangiopathy, diabetic macroangiopathy, cataracts and foot ulcers. Humans are especially preferred mammals which are treated by the methods of this invention.

Preferred ARIs for use in the combinations, pharmaceutical compositions, methods and kits of this invention include fidarestat, epalrestat, minalrestat, SPR-210, zenarastat or zopolrestat, prodrugs thereof and pharmaceutically acceptable salts of said ARIs and said prodrugs. It is especially preferred that said ARI is zopolrestat, a prodrug thereof or a pharmaceutically acceptable salt thereof or of said prodrug.

Preferred GABA agonists for use in the combinations, pharmaceutical compositions, methods and kits of this invention include: muscimol, progabide, riluzole, baclofen, gabapentin (Neurontin®), vigabatrin, valproic acid, tiagabine (Gabitril®), lamotrigine (Lamictal®), pregabalin, phenytoin (Dilantin®), carbamazepine (Tegretol®), topiramate (Topamax®), prodrugs thereof and pharmaceutically acceptable salts of said GABA agonists and said prodrugs.

More preferred GABA agonists for use in the combinations, pharmaceutical compositions, methods and kits of this invention include gabapentin, tiagabine, lamotrigine, phenytoin, carbamazepine, topiramate, pregabalin, prodrugs thereof and pharmaceutically acceptable salts of said GABA agonists and said prodrugs.

A particularly preferred GABA agonist for use in the combinations, pharmaceutical compositions, methods and kits of this invention is pregabalin, a prodrug thereof or a pharmaceutically acceptable salt of said pregabalin or said prodrug.

Another particularly preferred GABA agonist for use in the combinations, pharmaceutical compositions, methods and kits of this invention is gabapentin, a prodrug thereof or a pharmaceutically acceptable salt of said gabapentin or said prodrug.

DETAILED DESCRIPTION OF THE INVENTION

The combinations of this invention comprise two active components: a GABA agonist, a prodrug thereof or a pharmaceutically acceptable salt of said GABA agonist or said prodrug and an ARI, a prodrug thereof or a pharmaceutically acceptable salt of said ARI or said prodrug. The combinations of this invention optionally include a pharmaceutically acceptable vehicle, carrier or diluent.

The first component of the combinations of this invention is a GABA agonist, a prodrug thereof or a pharmaceutically acceptable salt of said GABA agonist or said prodrug. The term "GABA", where used in the description and the appendant claims, is synonymous with the term "γ-aminobutyric acid." These terms are used interchangeably throughout the description and appendant claims.

The GABA agonists suitable for use herein include, muscimol, progabide, riluzole, baclofen, gabapentin (Neurontin®), vigabatrin, valproic acid, tiagabine (Gabitril®), lamotrigine (Lamictal®), pregabalin (also known as (S)-isobutylgaba or (S)-3-(aminomethyl)-5-methylhexanoic acid), phenytoin (Dilantin®), carbamazepine (Tegretol®), topiramate (Topamax®), a prodrug thereof or a pharmaceutically acceptable salt of said GABA agonist or said prodrug. It will be recognized by those skilled in the art in light of this disclosure that other GABA agonists are also useful in the combinations, pharmaceutical compositions, methods and kits of this invention.

The GABA agonists disclosed herein are prepared by methods well known to those skilled in the art. Specifically, the following patents and patent applications, each of which is hereby incorporated herein by reference, exemplify GABA agonists which can be used in the combinations, pharmaceutical compositions, methods and kits of this invention, and refer to methods of preparaing those GABA agonists: U.S. Pat. No. 3,242,190 (specifically, muscimol); U.S. Pat. No. 4,094,992 (specifically, progabide); U.S. Pat. No. 4,370,338 (specifically, riluzole); U.S. Pat. No. 3,471,548 (specifically, baclofen); U.S. Pat. No. 4,024,175 (specifically, gabapentin); U.S. Pat. No. 3,960,927 (specifically, vigabatrin); U.S. Pat. No. 5,010,090 (specifically, tiagabine); U.S. Pat. No. 4,602,017 (specifically, lamotrigine); U.S. Pat. No. 6,028,214 (specifically, pregabalin); U.S. Pat. No. 2,409,754 (specifically, phenytoin) and U.S. Pat. No. 4,513,006 (specifically, topiramate). Valproic acid is prepared as disclosed in Carraz et al., Therapie, 1965, 20, 419.

The structures of the preferred GABA agonists are set forth in Scheme I below.

Scheme I

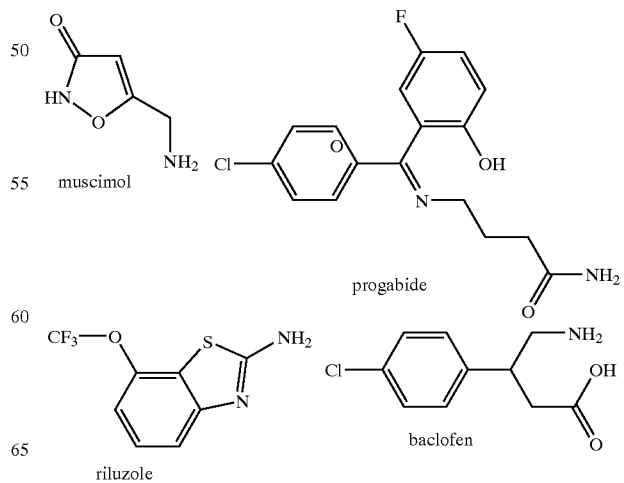

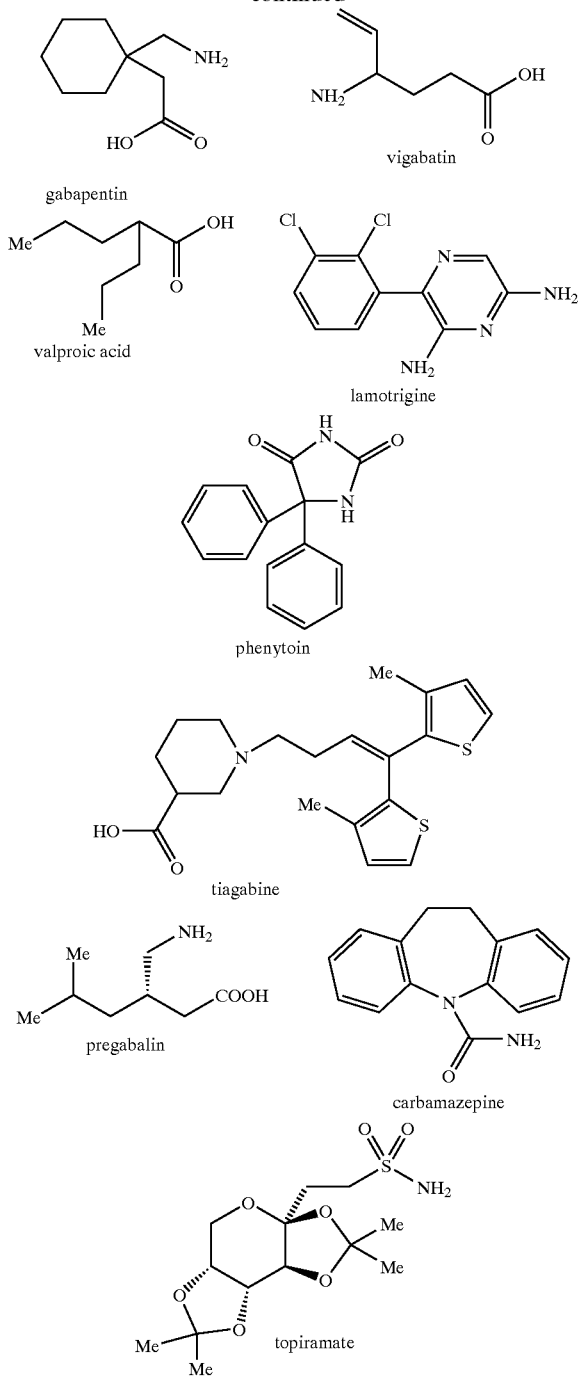

Any ARI may be used as one of the active ingredients in the combinations, pharmaceutical compositions, methods and kits of the instant invention. The term aldose reductase inhibitor refers to a compound which inhibits the bioconversion of glucose to sorbitol catalyzed by the enzyme aldose reductase. Such inhibition is readily determined by those skilled in the art according to standard assays (J. Malone, *Diabetes*, 29:861–864, 1980. "Red Cell Sorbitol, an Indicator of Diabetic Control"). The following patents and patent applications, each of which is hereby incorporated herein by reference, exemplify aldose reductase inhibitors which can be used in the compositions, methods and kits of this invention, and refer to methods of preparing those aldose reductase inhibitors: U.S. Pat. No. 4,251,528; U.S. Pat. No. 4,600,724; U.S. Pat. No. 4,464,382, U.S. Pat. No. 4,791,126, U.S. Pat. No. 4,831,045; U.S. Pat. No. 4,734,419; 4,883,800; U.S. Pat. No. 4,883,410; U.S. Pat. No. 4,883,410; U.S. Pat. No. 4,771,050; U.S. Pat. No. 5,252,572; U.S. Pat. No. 5,270,342; U.S. 5,430,060; U.S. Pat. No. 4,130,714; U.S. Pat. No. 4,540,704; U.S. Pat. No. 4,438,272; U.S. Pat. No. 4,436,745, U.S. Pat. No. 4,438,272; U.S. Pat. No. 4,436,745, U.S. Pat. No. 4,438,272; U.S. Pat. No. 4,436,745, U.S. Pat. No. 4,438,272; U.S. Pat. No. 4,980,357; U.S. Pat. No. 5,066,659; U.S. Pat. No. 5,447,946; U.S. Pat. No. 5,037,831.

A variety of aldose reductase inhibitors are specifically described and referenced below, however, other aldose reductase inhibitors will be known to those skilled in the art. Also, common chemical USAN names or other designations are in parentheses where applicable, together with reference to appropriate patent literature disclosing the compound.

Accordingly, examples of aldose reductase inhibitors useful in the compositions, methods and kits of this invention include:

1. 3-(4-bromo-2-fluorobenzyl)-3,4-dihydro-4-oxo-1-phthalazineacetic acid (ponalrestat, U.S. Pat. No. 4,251,528);
2. N[[(5-trifluoromethyl)-6-methoxy-1-naphthalenyl]thioxomethyl}-N-methylglycine (tolrestat, U.S. Pat. No. 4,600,724);
3. 5-[(Z,E)-β-methylcinnamylidene]-4-oxo-2-thioxo-3-thiazolideneacetic acid (epalrestat, U.S. Pat. No. 4,464,382, U.S. Pat. No. 4,791,126, U.S. Pat. No. 4,831,045);
4. 3-(4-bromo-2-fluorobenzyl)-7-chloro-3,4-dihydro-2,4-dioxo-1 (2H)-quinazolineacetic acid (zenarestat, U.S. Pat. No. 4,734,419, and U.S. Pat. No. 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);
9. N-[3,5-dimethyl-4-[(nitromethyl)sulfonyl]phenyl]-2-methyl-benzeneacetamide (ZD5522, U.S. Pat. No. 5,270,342 and U.S. Pat. No. 5,430,060);
10. (S)-6-fluorospiro[chroman-4,4'-imidazolidine]-2,5'-dione (sorbinil, U.S. Pat. No. 4,130,714);
11. d-2-methyl-6-fluoro-spiro(chroman-4',4'-imidazolidine)-2',5'-dione (U.S. Pat. No. 4,540,704);
12. 2-fluoro-spiro(9H-fluorene-9,4'-imidazolidine)-2',5'-dione (U.S. Pat. No. 4,438,272);
13. 2,7-di-fluoro-spiro(9H-fluorene-9,4'-imidazolidine)-2',5'-dione (U.S. Pat. No. 4,436,745, U.S. Pat. No. 4,438,272);
14. 2,7-di-fluoro-5-methoxy-spiro(9H-fluorene-9,4'-imidazolidine)-2',5'-dione (U.S. Pat. No. 4,436,745, U.S. Pat. No. 4,438,272);
15. 7-fluoro-spiro(5H-indenol[1,2-b]pyridine-5,3'-pyrrolidine)-2,5'-dione (U.S. Pat. No. 4,436,745, U.S. Pat. No. 4,438,272);
16. d-cis-6'-chloro-2',3'-dihydro-2'-methyl-spiro-(imidazolidine-4,4'-4'H-pyrano(2,3-b)pyridine)-2,5-dione (U.S. Pat. No. 4,980,357);

17. spiro[imidazolidine-4,5'(6H)-quinoline]-2,5-dione-3'-chloro-7',8'-dihydro-7'-methyl-(5'-cis) (U.S. Pat. No. 5,066,659);
18. (2S,4S)-6-fluoro-2',5'-dioxospiro(chroman-4,4'-imidazolidine)-2-carboxamide (fidarestat, U.S. Pat. No. 5,447,946); and
19. 2-[(4-bromo-2-fluorophenyl)methyl]-6-fluorospiro[isoquinoline-4(1 H),3'-pyrrolidine]-1,2',3,5'(2H)-tetrone (minalrestat, U.S. Pat. No. 5,037,831).

Other aldose reductase inhibitors include compounds of formula A,

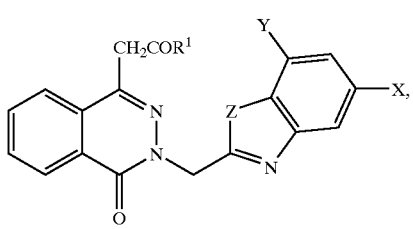

and pharmaceutically acceptable salts thereof, wherein
Z is O or S;
$R^1$ is hydroxy or a group capable of being removed in vivo to produce a compound of formula A wherein $R^1$ is OH; and
X and Y are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of formula A:

20. 3,4-dihydro-3-(5-fluorobenzothiazol-2-ylmethyl)-4-oxophthalazin-1-yl-acetic acid [$R^1$=hydroxy; X=F; Y=H];
21. 3-(5,7-difluorobenzothiazol-2-ylmethyl)-3,4-dihydro-4-oxophthalazin-1-ylacetic acid [$R^1$=hydroxy; X=Y=F];
22. 3-(5-chlorobenzothiazol-2-ylmethyl)-3,4-dihydro-4-oxophthalazin-1-ylacetic acid [$R^1$=hydroxy; X=Cl; Y=H];
23. 3-(5,7-dichlorobenzothiazol-2-ylmethyl)-3,4-dihydro-4-oxophthalazin-1-ylacetic acid [$R^1$=hydroxy; X=Y=Cl];
24. 3,4-dihydro-4-oxo-3-(5-trifluoromethylbenzoxazol-2-ylmethyl)phthalazin-1-ylacetic acid [$R^1$=hydroxy; X=$CF_3$; Y=H];
25. 3,4-dihydro-3-(5-fluorobenzoxazol-2-ylmethyl)-4-oxophthalazin-1-yl-acetic acid [$R^1$=hydroxy; X=F; Y=H];
26. 3-(5,7-difluorobenzoxazol-2-ylmethyl)-3,4-dihydro-4-oxophthalazin-1-ylacetic acid [$R^1$=hydroxy; X=Y=F];
27. 3-(5-chlorobenzoxazol-2-ylmethyl)-3,4-dihydro-4-oxophthalazin-1-ylacetic acid [$R^1$=hydroxy; X=Cl; Y=H];
28. 3-(5,7-dichlorobenzoxazol-2-ylmethyl)-3,4-dihydro-4-oxophthalazin-1-ylacetic acid [$R^1$=hydroxy; X=Y=Cl]; and
29. zopolrestat; 1-phthalazineacetic acid, 3,4-dihydro-4-oxo-3-[[5-(trifluoromethyl)-2-benzothiazolyl]methyl]- [$R^1$=hydroxy; X=trifluoromethyl; Y=H].

In compounds 20–23 and 29, Z is S. In compounds 24–28, Z is O.

Said compounds of formula A are prepared as disclosed in U.S. Pat. No. 4,939,140.

The aldose reductase inhibitor compounds of this invention are readily available or can be easily synthesized by those skilled in the art using conventional methods of organic synthesis, particularly in view of the pertinent patent specifications.

It will be recognized that certain of the GABA agonists and ARIs used in the pharmaceutical compositions, methods and kits of this invention contain either a free carboxylic acid or a free amine group as part of the chemical structure. Thus, this invention includes pharmaceutically acceptable salts of those carboxylic acids or amine groups. The expression "pharmaceutically acceptable salts" includes both pharmaceutically acceptable acid addition salts and pharmaceutically acceptable cationic salts. The expression "pharmaceutically-acceptable cationic salts" is intended to define but is not limited to such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically-acceptable acid addition salts" is intended to define but is not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

The pharmaceutically-acceptable cationic salts of GABA agonists or ARIs containing free carboxylic acids may be readily prepared by reacting the free acid form of the GABA agonists or ARIs with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (e.g., sodium or potassium ethylhexanoate, magnesium oleate), employing a solvent (e.g., ethyl acetate) from which the desired cationic salt precipitates, or can be otherwise isolated by concentration and/or addition of a non-solvent.

The pharmaceutically acceptable acid addition salts of GABA agonists or ARIs containing free amine groups may be readily prepared by reacting the free base form of the GABA agonist or ARI with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The expression "prodrug" refers to compounds that are drug precursors which, following administration, release the drug in vivo via some chemical or physiological process (e.g., a prodrug on being brought to the physiological pH or through enzyme action is converted to the desired drug form). Both the GABA agonists and the ARIs used in the combinations, pharmaceutical compositions, methods and kits of this invention may be prepared as prodrugs. The preparation of prodrugs is straightforward and may be achieved using methods well known to those skilled in the art. All such prodrugs are within the scope of the combinations, pharmaceutical compositions, methods and kits of this invention.

The chemist of ordinary skill in the art will also recognize that certain compounds within the scope of this invention can exist in tautomeric form, i.e., that an equilibrium exists between two isomers which are in rapid equilibrium with each other. A common example of tautomerism is keto-enol tautomerism, i.e.,

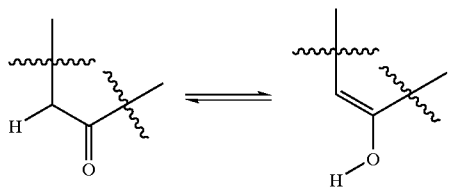

Examples of compounds which can exist as tautomers include hydroxypyridines, hydroxypyrimidines and hydroxyquinolines. Other examples will be recognized by those skilled in the art. All such tautomers and mixtures thereof are included in this invention.

The chemist of ordinary skill in the art will also recognize that certain compounds within the scope of this invention can exist in zwitterionic form, i.e., that certain compounds contain an amine portion and a carboxylic acid portion, which, depending upon the pH of the solution, may exist as a free amine and a free carboxylic acid or as a zwitterion in which the amine is protonated to form an ammonium ion and the carboxylic acid is deprotonated to form a carboxylate ion. All such zwitterions are included in this invention. In addition, the GABA agonists, prodrugs thereof and pharmaceutically acceptable salts of said GABA agonists and said prodrugs used in the combinations of the instant invention may occur as hydrates or solvates. Further, the ARIs, prodrugs thereof and pharmaceutically acceptable salts of said ARIs and said prodrugs used in the combinations of the instant invention may also occur as hydrates or solvates. Said hydrates and solvates are also within the scope of the invention.

Methods for determining the aldose reductase inhibiting activity of the ARIs used in the combinations, pharmaceutical compositions, methods and kits of this invention are well known and may be achieved by following the procedures disclosed, for example, in Mylari et al., J. Med. Chem., 34, 108, (1991). Methods for determining the GABA agonist activity of the GABA agonists used in the combinations, pharmaceutical compositions, methods and kits of this invention are well known and may be achieved by following the procedures disclosed, for example, in Janssens de Verebeke, P. et al., Biochem. Pharmacol., 31, 2257–2261 (1982), Loscher, W., Biochem. Pharmacol., 31, 837–842, (1982) and/or Phillips, N. et al., Biochem. Pharmacol., 31, 2257–2261.

The above assays demonstrating the effectiveness of ARIs, prodrugs thereof and pharmaceutically acceptable salts of said ARIs and said prodrugs, and GABA agonists, prodrugs thereof and pharmaceutically acceptable salts of said GABA agonists and said prodrugs in the treatment of diabetic complications also provide a means whereby the activities of the compounds of this invention can be compared between themselves and with the activities of other known compounds. The results of these comparisons are useful for determining dosage levels in mammals, including humans, for the treatment of such diseases.

The effect of a pharmaceutical composition comprising a GABA agonist and an ARI of the present invention may be examined by using one or more of the published models of diabetic complications well known in the art. The pharmaceutical compositions of the present invention are particularly useful for the prevention of, reducing the development of, or reversal of, deficits in nerve function found in diabetic patients, and therefore are particularly useful in the treatment of diabetic neuropathy. This may be demonstrated, for example, by measuring markers such as nerve conduction velocity, nerve amplitude, quantitative sensory testing, autonomic function testing and morphometric changes. Studies analogous to those described in Diabetologia, 1992, Vol. 35, pages 12–18 and 1994, Vol. 37, pages 651–663 may be carried out.

In general, the ARIs used in the combinations, pharmaceutical compositions, methods and kits of this invention and their pharmaceutically acceptable salts, will be administered at dosages between about 0.001 and about 100 mg/kg body weight of the subject to be treated per day, preferably from about 0.01 mg/kg to about 10 mg/kg, in single or divided doses. However, some variation in dosage will necessarily occur depending upon the condition of the subject being treated. The person responsible for administration will, in any event, determine the appropriate dose for the individual subject.

The following dosage amounts and other dosage amounts set forth elsewhere in this description and in the appendant claims are for an average human subject having a weight of about 65 kg to about 70 kg. The skilled practitioner will readily be able to determine the dosage amount required for a subject whose weight falls outside the 65 kg to 70 kg range, based upon the medical history of the subject. All doses set forth herein, and in the appendant claims, are daily doses.

In general, in accordance with this invention, the above GABA agonists used in the combinations, pharmaceutical compositions, methods and kits of this invention will be administered in a dosage amount of about 4 mg/kg body weight of the subject to be treated per day to about 60 mg/kg body weight of the subject to be treated per day, in single or divided doses. However, some variation in dosage will necessarily occur depending upon the condition of the subject being treated. The person responsible for administration will, in any event, determine the appropriate dose for the individual subject. In particular, when used as the GABA agonist in this invention, pregabalin will be dosed at about 300 mg to about 1200 mg per day; gabapentin will be dosed at about 600 mg to about 3600 mg per day.

It will be recognized by a skilled person that the free base form or other salt forms of the above GABA agonists and ARIs may be used in this invention. Calculation of the dosage amount for these other forms of the free base form or other salt forms of a particular GABA agonist or ARI is easily accomplished by performing a simple ratio relative to the molecular weights of the species involved.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

The combinations of this invention may also be administered in a controlled release formulation such as a slow release or a fast release formulation. Such controlled release formulations of the combinations of this invention may be prepared using methods well known to those skilled in the art. The method of adminstration will be determined by the attendant physician or other person skilled in the art after an evaluation of the subject's condition and requirements.

The combinations of this invention may also be administered in parenteral form. For parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

Methods of preparing various pharmaceutical compositions with a certain amount of active ingredient are known, or will be apparent in light of this disclosure, to those skilled in this art. For examples, see *Remington: The Science and Practice of Pharmacy*, Mack Publishing Company, Easton, Pa., 19th Edition (1995).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the condition or disease of the subject being treated.

The two different compounds of this invention can be co-administered simultaneously or sequentially in any order, or as a single pharmaceutical composition comprising an ARI and a GABA agonist as described above.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: an ARI, a prodrug thereof or a pharmaceutically acceptable salt of said ARI or prodrug and a GABA agonist, a prodrug thereof or a pharmaceutically acceptable salt of said GABA agonist or prodrug. The kit comprises a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of the ARI can consist of one tablet or capsule while a daily dose of the GABA agonist can consist of several tablets or capsules or vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

It should be understood that the invention is not limited to the particular embodiments described herein, but that various changes and modifications may be made without departing from the spirit and scope of this novel concept as defined by the following claims.

What is claimed is:

1. A method of treating a diabetic complication in a mammal comprising administering to said mammal in need of such treatment
   (a) an amount of a first compound, said first compound being a GABA agonist or a pharmaceutically acceptable salt of said GABA agonist; and
   (b) an amount of a second compound, said second compound being an aldose reductase inhibitor or a pharmaceutically acceptable salt of said ARI
   wherein said first compound and said second compound are each optionally and independently administered together with a pharmaceutically acceptable vehicle, carrier or diluent.

2. A method of claim 1 wherein said GABA agonist is muscimol, progabide, riluzole, baclofen, gabapentin, vigabatrin, valproic acid, tiagabine, lamotrigine, pregabalin, phenytoin, carbamazepine, topiramate or a pharmaceutically acceptable salt of said GABA agonist.

3. A method of claim 2 wherein said GABA agonist is gabapentin, tiagabine, lamotrigine, phenytoin, carbamazepine, topiramate, pregabalin or a pharmaceutically acceptable salt of said GABA agonist.

4. A method of claim 3 wherein said GABA agonist is pregabalin or a pharmaceutically acceptable salt thereof.

5. A method of claim 3 wherein said GABA agonist is gabapentin or a pharmaceutically acceptable salt thereof.

6. A method of claim 1 wherein said aldose reductase inhibitor is fidarestat, epalrestat, minalrestat, SPR-210, zenarestat, zopolrestat or a pharmaceutically acceptable salt of said aldose reductase inhibitor.

7. A method of claim 1 wherein said diabetic complication is diabetic neuropathy, diabetic nephropathy, diabetic retinopathy, diabetic cardiomyopathy, diabetic microangiopathy, diabetic macroangiopathy, cataracts or foot ulcers.

8. A method of treating a diabetic complication in a mammal comprising administering to said mammal in need of such treatment a pharmaceutical composition comprising
    (a) an amount of a first compound, said first compound being a GABA agonist or a pharmaceutically acceptable salt of said GABA agonist; and
    (b) an amount of a second compound, said second compound being an aldose reductase inhibitor or a pharmaceutically acceptable salt of said ARI.

9. A method of claim 8 wherein said pharmaceutical composition additionally comprises a pharmaceutically acceptable vehicle, carrier or diluent.

10. A method of claim 8 wherein said diabetic complication is diabetic neuropathy, diabetic nephropathy, diabetic retinopathy, diabetic cardiomyopathy, diabetic microangiopathy, diabetic macroangiopathy, cataracts or foot ulcers.

11. A pharmaceutical composition comprising:
    a. an amount of a GABA agonist or a pharmaceutically acceptable salt of said GABA agonist; and
    b. an amount of an ARI or a pharmaceutically acceptable salt of said ARI.

12. A pharmaceutical composition of claim 11 additionally comprising a pharmaceutically acceptable vehicle, carrier or diluent.

13. A pharmaceutical composition of claim 12 wherein said GABA agonist is muscimol, progabide, riluzole, baclofen, gabapentin, vigabatrin, valproic acid, tiagabine, lamotrigine, pregabalin, phenytoin, carbamazepine, topiramate, or a pharmaceutically acceptable salt of said GABA agonist.

14. A pharmaceutical composition of claim 13 wherein said GABA agonist is gabapentin, tiagabine, lamotrigine, phenytoin, carbamazepine, topiramate, pregabalin, or a pharmaceutically acceptable salt of said GABA agonist.

15. A pharmaceutical composition of claim 14 wherein said GABA agonist is pregabalin or a pharmaceutically acceptable salt of said pregabalin.

16. A pharmaceutical composition of claim 14 wherein said GABA agonist is gabapentin or a pharmaceutically acceptable salt of said gabapentin.

17. A pharmaceutical composition of claim 12 wherein said ARI is fidarestat, epalrestat, minalrestat, SPR-210, zenarestat, zopoir stat, or a pharmaceutically acceptable salt of said ARI.

18. A pharmaceutical composition of claim 17 wherein said GABA agonist is muscimol, progabide, riluzole, baclofen, gabapentin, vigabatrin, valproic acid, tiagabine, lamotrigine, pregabalin, phenytoin, carbamazepine, topiramate, or a pharmaceutically acceptable salt of said GABA agonist.

19. A pharmaceutical composition of claim 18 wherein said GABA agonist is gabapentin, tiagabine, lamotrigine, phenytoin, carbamazepine, topiramate and pregabalin, or a pharmaceutically acceptable salt of said GABA agonist.

20. A pharmaceutical composition of claim 19 wherein said GABA agonist is pregabalin or a pharmaceutically acceptable salt of said pregabalin.

21. A pharmaceutical composition of claim 19 wherein said GABA agonist is gabapentin or a pharmaceutically acceptable salt of said gabapentin.

22. A kit for achieving a therapeutic effect in a mammal comprising:
    a. an amount of a GABA agonist, or a pharmaceutically acceptable salt of said GABA agonist, and a pharmaceutically acceptable vehicle, carrier or diluent in a first unit dosage form;
    b. an amount of an ARI, or a pharmaceutically acceptable salt of said ARI, and a pharmaceutically acceptable vehicle, carrier or diluent in a second unit dosage form; and
    c. a container.

23. A method for treating a mammal in need of therapeutic treatment comprising administering to said mammal
    (a) an amount of a first compound, said first compound being a GABA agonist or a pharmaceutically acceptable salt of said GABA agonist; and
    (b) an amount of a second compound, said second compound being an ARI or a pharmaceutically acceptable salt of said ARI wherein said first compound and said second compound are each optionally and independently administered together with a pharmaceutically acceptable vehicle, carrier or diluent.

24. A method of claim 23 wherein said GABA agonist is muscimol, progabide, riluzole, baclofen, gabapentin, vigabatrin, valproic acid, tiagabine, lamotrigine, pregabalin, phenytoin, carbamazepine, topiramate, or a or a pharmaceutically acceptable salt of said GABA agonist.

25. A method of claim 24 wherein said GABA agonist is gabapentin, tiagabine, lamotrigine, phenytoin, carbamazepine, topiramate, pregabalin, pharmaceutically acceptable salt of said GABA agonist.

26. A method of claim 25 wherein said GABA agonist is pregabalin or a pharmaceutically acceptable salt of said pregabalin.

27. A method of claim 25 wherein said GABA agonist is gabapentin or a pharmaceutically acceptable salt of said gabapentin.

* * * * *